United States Patent
Nakazato et al.

(10) Patent No.: US 6,770,676 B2
(45) Date of Patent: Aug. 3, 2004

(54) DICARBOXYLIC ACID DERIVATIVES

(75) Inventors: Atsuro Nakazato, Satte (JP); Toshihito Kumagai, Saitama (JP); Kosuke Kanuma, Kazo (JP); Kazunari Sakagami, Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 51 days.

(21) Appl. No.: 10/297,479
(22) PCT Filed: Jun. 28, 2001
(86) PCT No.: PCT/JP01/05550
§ 371 (c)(1),
(2), (4) Date: Dec. 6, 2002
(87) PCT Pub. No.: WO02/00605
PCT Pub. Date: Jan. 3, 2002

(65) Prior Publication Data
US 2003/0134902 A1 Jul. 17, 2003

(30) Foreign Application Priority Data
Jun. 28, 2000 (JP) ........................ 2000-195239

(51) Int. Cl.[7] ................. C07C 61/13; A61K 31/19; A61K 31/21
(52) U.S. Cl. .............. 514/561; 560/119; 560/122; 560/124; 560/125; 560/116; 562/501; 514/510
(58) Field of Search .................. 560/122, 124, 560/125, 116, 119; 514/561

(56) References Cited

U.S. PATENT DOCUMENTS 5,916,920 A * 6/1999 Fernandez et al. .......... 514/561

FOREIGN PATENT DOCUMENTS

WO 2000/012464 A1 9/2000

* cited by examiner

Primary Examiner—D. Margaret Seaman
Assistant Examiner—Taylor Victor Oh
(74) Attorney, Agent, or Firm—Lorusso, Loud & Kelly

(57) ABSTRACT

The present invention relates to 2-amino-6-fluorobicyclo[3.1.0]hexane-2,6-dicarboxylic acid derivatives represented by the formula:

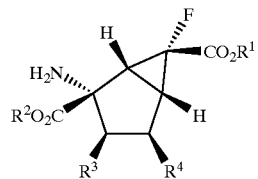

the pharmaceutically acceptable salts thereof, or the hydrates thereof. The compounds of the present invention are useful as a medicament, and in particular, are useful as modulators acting on group 2 metabotropic glutamate receptors, having effects for treating and/or preventing psychiatric disorders such as schizophrenia, anxiety and its associated diseases, depression, bipolar disorder, and epilepsy; and/or neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

6 Claims, No Drawings

DICARBOXYLIC ACID DERIVATIVES

TECHNICAL FIELD

The present invention relates to 2-amino-6-fluorobicyclo[3.1.0]hexane-2,6-dicarboxylic acid derivatives that are useful as a medicament. In particular, it relates to novel 2-amino-6-fluorobicyclo[3.1.0]hexane-2,6-dicarboxylic acid derivatives which exhibit treatment effects and/or prevention effects on psychiatric disorders such as schizophrenia, anxiety and its associated diseases, depression, bipolar disorder, and epilepsy; and/or on neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

BACKGROUND ART

In recent years, with the repeated cloning of glutamate receptor genes, it has become clear that there are surprisingly many subtypes of glutamate receptors. At present, glutamate receptors are roughly classified into two types: the "ionotropic type", in which the receptor has an ion channel type structure, and the "metabotropic type", in which the receptor is coupled to G-proteins (*Science*, 258, 597–603, 1992). In addition, ionotropic receptors are classified pharmacologically into three types: NMDA, α-amino-3-hydroxy-5-methyl isoxazole-4-propionate (AMPA), and kainate (*Science*, 258, 597–603, 1992). Metabotropic receptors are classified into eight types, type 1 through type 8 (*J. Neurosci.*, 13, 1372–1378, 1993; and *Neuropharmacol.*, 34, 1–26, 1995).

The metabotropic glutamate receptors are classified pharmacologically into three groups. Of these, group 2 (mGluR2/mGluR3) bind with adenylcyclase, and inhibit the accumulation of the Forskolin stimulation of cyclic adenosine monophosphate (cAMP) (*Trends Pharmacol. Sci.*, 14, 13 (1993)), and for this reason, it is suggested that the compounds acting on group 2 metabotropic glutamate receptors should be useful for the treatment or prevention of acute and chronic psychiatric disorders and neurological diseases.

DISCLOSURE OF THE INVENTION

An object of the present invention is to provide a medicament acting on group 2 metabotropic glutamate receptors, which has the treatment effects and/or prevention effects on psychiatric disorders such as schizophrenia, anxiety and its associated diseases, depression, bipolar disorder, and epilepsy; and/or on neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

As a result of a diligent research with regard to 2-amino-6-fluorobicyclo[3.1.0]hexane-2,6-dicarboxylic acid derivatives and ester derivatives thereof, the present inventors discovered novel 2-amino-6-fluorobicyclo[3.1.0]hexane-2,6-dicarboxylic acid derivatives and ester derivatives thereof, which act on group 2 metabotropic glutamate receptors, and have consequently, completed the present invention.

One mode of the present invention relates to a 2-amino-6-fluoro-bicyclo[3.1.0]hexane-2,6-dicarboxylic acid derivative represented by the formula [I]:

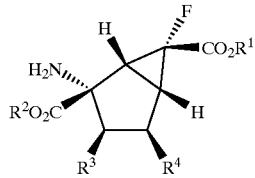

[1]

(wherein, $R^1$ and $R^2$ are the same or different, and each represents a hydrogen atom, a $C_{1-10}$ alkyl group, a $C_{3-8}$ cycloalkyl group, a $C_{3-8}$ cycloalkyl $C_{1-6}$ alkyl group, an aryl group, an aryl $C_{1-6}$ alkyl group, a $C_{1-6}$ alkoxy $C_{1-6}$ alkyl group, an $C_{1-6}$ hydroxyalkyl group, a $C_{1-6}$ alkylthio $C_{1-6}$ alkyl group, a $C_{1-6}$ mercaptoalkyl group, a tetrahydrofuranyl group, or a tetrahydropyranyl group;

in $R^3$ and $R^4$, when $R^3$ is a hydroxyl group, $R^4$ is a hydrogen atom; alternatively, $R^3$ and $R^4$ together form a C—C single bond), a pharmaceutically acceptable salt thereof.

Another mode of the present invention relates to a medicament comprising the compound represented by the formula [I] or a pharmaceutically acceptable salt thereof as an active ingredient, and in particular, relates to an agent for treating or preventing psychiatric disorders or neurological diseases, as well as relates to a group 2 metabotropic glutamate receptor modulator.

Another mode of the present invention relates to use of the compound represented by the formula [I] or a pharmaceutically acceptable salt thereof, for the manufacture of a group 2 metabotropic glutamate receptor modulator, and for the manufacture of an agent for treating and/or preventing psychiatric disorders and/or neurological diseases.

The terms used in the present invention are defined below. In the present invention, "$C_{n-m}$" means that the group following the "$C_{n-m}$" has a number of carbon atoms n to m.

The $C_{1-10}$ alkyl group means a straight-chain or branched-chain alkyl group, examples of which include a methyl group, an ethyl group, a propyl group, an isopropyl group, a butyl group, an isobutyl group, a t-butyl group, a pentyl group, an isopentyl group, a 1-ethylpropyl group, a hexyl group, an isohexyl group, a 2-ethylbutyl group, a heptyl group, an isoheptyl group, an octyl group, a nonyl group, a decyl group, and the like.

The $C_{3-8}$ cycloalkyl group means, for example, a cyclopropyl group, a cyclobutyl group, a cyclopentyl group, a cyclohexyl group, and the like.

The $C_{3-8}$ cycloalkyl $C_{1-6}$ alkyl group means, for example, a cyclopropylmethyl group, a cyclobutylmethyl group, a cyclopentylmethyl group, a cyclohexylmethyl group, and the like.

The aryl group means a phenyl group, a naphthyl group, or the like, and preferably means a phenyl group. The aryl $C_{1-6}$ alkyl group means a straight-chain or branched-chain $C_{1-6}$ alkyl group substituted with at least one aryl group, and preferably at least one phenyl group. Examples thereof include, for example, a benzyl group, a diphenylmethyl group, a 1-phenylethyl group, a 2-phenylethyl group, and the like.

The $C_{1-6}$ alkoxy $C_{1-6}$ alkyl group means a group having a combined structure of a $C_{1-6}$ alkoxy group and a $C_{1-6}$ alkyl group. The $C_{1-6}$ alkoxy group means a straight-chain or branched-chain alkoxy group, examples of which include a methoxy group, an ethoxy group, a propoxy group, an isopropoxy group, a butoxy group, an isobutoxy group, a t-butoxy group, a pentyloxy group, an isopentyloxy group, or the like. Therefore, examples of the $C_{1-6}$ alkoxy $C_{1-6}$ alkyl group include a methoxymethyl group, an ethoxymethyl group, a methoxyethyl group, an ethoxyethyl group, a propoxyethyl group, an isopropoxyethyl group, a butoxyethyl group, an isobutoxyethyl group, a pentyloxyethyl group, an isopentyloxyethyl group, and the like.

The $C_{1-6}$ hydroxyalkyl group means a $C_{1-6}$ alkyl group substituted with at least one hydroxyl group. Therefore, examples of the $C_{1-6}$ hydroxyalkyl group include a 2-hydroxyethyl group, a 3-hydroxypropyl group, a 2,3-dihydroxypropyl group, and the like.

The $C_{1-6}$ alkylthio $C_{1-6}$ alkyl group means a group having a combined structure of a $C_{1-6}$ alkylthio group and a $C_{1-6}$ alkyl group. The $C_{1-6}$ alkylthio group means a straight-chain or branched-chain alkylthio group, examples of which include a methylthio group, an ethylthio group, a propylthio group, an isopropylthio group, a butylthio group, an isobutylthio group, a t-butylthio group, a pentylthio group, an isopentylthio group, and the like. Therefore, examples of the $C_{1-6}$ alkylthio $C_{1-6}$ alkyl group include a methylthiomethyl group, a 2-methylthioethyl group, and the like.

The $C_{1-6}$ mercaptoalkyl group means a $C_{1-6}$ alkyl group substituted with at least one mercapto group. Therefore, examples of the $C_{1-6}$ mercaptoalkyl include a 2-mercaptoethyl group, a 3-mercaptopropyl group, a 2,3-dimercaptopropyl group, and the like.

In addition, a pharmaceutically acceptable salt in the present invention refers to, for example, a salt with an inorganic acid such as sulfuric acid, hydrochloric acid, or phosphoric acid; a salt with an organic acid such as acetic acid, oxalic acid, lactic acid, tartaric acid, fumaric acid, maleic acid, methanesulfonic acid, or benzenesulfonic acid; a salt with an amine such as trimethylamine, or methylamine; or a salt with a metal ion such as sodium ion, potassium ion, or calcium ion.

The compounds represented by the formula [I] have four or five asymmetric carbon atoms. Therefore, the compounds of the present invention can be present as optically active substances, enantiomers thereof, or an enantiomer mixture such as racemic body. That is, the compounds of the present invention include all the optically active substances of the compounds represented by the formula [I], enantiomers thereof, an enantiomer mixture such as racemic body, and a diastereomer mixture. In the formula [I], the compounds, wherein $R^3$ represents a hydroxyl group, and $R^4$ represents a hydrogen atom, are preferable. Furthermore, in the formula [I], the compounds, wherein $R^1$, $R^2$, and $R^4$ represent a hydrogen atom, and $R^3$ represents a hydroxyl group, are more preferable. (1R,2R,3R,5R,6R)-2-amino-6-fluoro-3-hydroxy-bicyclo[3.1.0]hexane-2,6-dicarboxylic acid is particularly preferable. In addition, the compounds of the present invention can be present as various solvates, and hydrates are preferable from the standpoint of applicability as a medicament.

In addition, in the formula [I], if both of $R^1$ and $R^2$ or one of $R^1$ and $R^2$ do not represent a hydrogen atom, that is, in the case of the ester derivatives, the ester derivatives do not act on group 2 metabotropic glutamate receptors. However, the ester derivatives are subjected to hydrolysis in vivo, and as a result, they are converted into the carboxylic acids which can act on group 2 metabotropic glutamate receptors. Therefore, the ester derivatives function as prodrugs, and for this reason, they are extremely useful compounds.

The compounds of the formula [I] can be produced according to the preparation methods described below (in the following reaction schemes, $R^1$, $R^2$, $R^3$, and $R^4$ have the same meanings as described above).

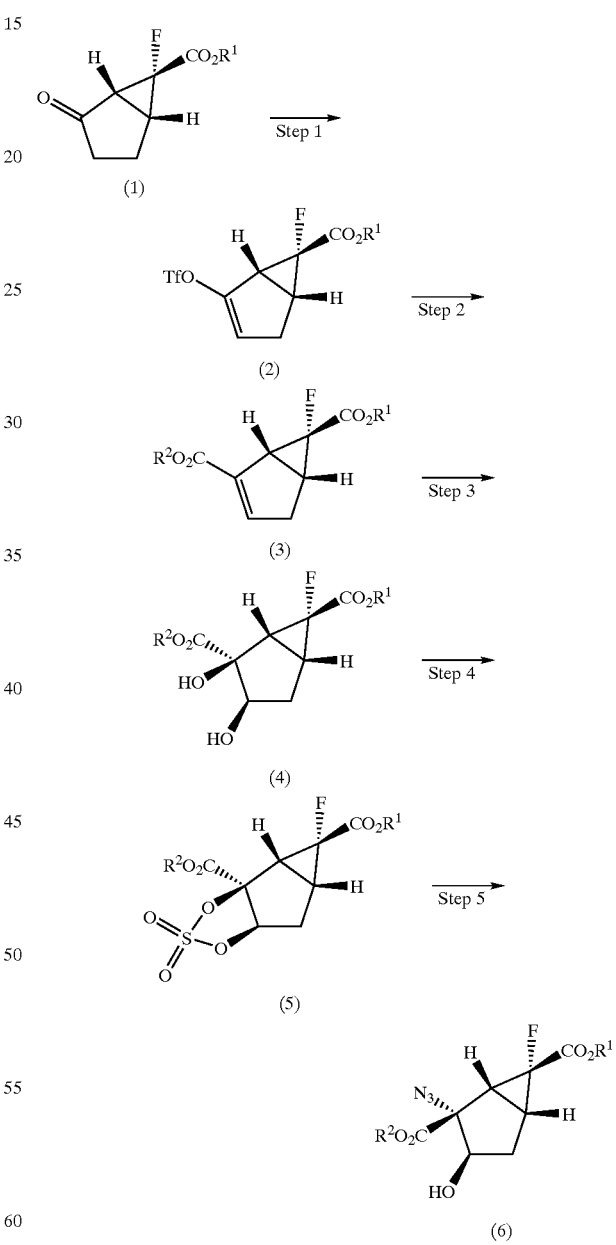

Step 1: First, Compound (1) is transformed into Compound (2) by means of the reaction with a trifluoromethane-sulfonylation agent, such as trifluoroacetic anhydride, N-phenyl-bis(trifluoromethanesulfonimide), or the like, in the presence of a base in an inert solvent.

In this step, as the inert solvent, for example, hydrocarbon type solvents such as benzene, toluene, and hexane; halogen type solvents such as dichloromethane and chloroform; ether type solvents such as tetrahydrofuran, diethyl ether, and 1,2-dimethoxyethane; acetonitrile; a mixture of these solvents; or the like can be employed.

In addition, as the base, for example, amines such as triethylamine, N-methylmorpholine, diisopropylethylamine, and pyridine; inorganic bases such as potassium hydride and sodium hydride; metal amides such as lithium diisopropylamide and potassium bis(trimethylsilyl)amide; or metal alcholates such as sodium methoxide and potassium t-butoxide can be employed.

Step 2: Next, Compound (2) is transformed into Compound (3) by means of the reaction with carbon oxide and $R^2OH$ in the presence of a transition metal catalyst, and in the presence of organic bases such as triethylamine, N-methylmorpholine, diisopropylethylamine, and pyridine, or of inorganic bases such as potassium carbonate and sodium hydrogencarbonate, in an inert solvent (see *J. Org. Chem.* 57, 5979 (1992)).

In this step, the transition metal catalyst means, for example, a palladium (0) reagent, and can be prepared in the reaction system by employing, for example, a divalent palladium such as palladium (II) acetate, and a ligand such as triphenylphosphine or 2,2'-bis(diphenylphosphino)-1,1'-binaphthyl (BINAP). In addition, a palladium (0) catalyst such as tetrakis(triphenylphosphine) palladium (0) can be directly employed.

In addition, as the inert solvent, for example, hydrocarbon type solvents such as benzene, toluene, and hexane; ether type solvents such as tetrahydrofuran, diethyl ether, and 1,2-dimethoxyethane; acetonitrile; a mixture of these solvents; or the like can be employed.

Step 3: Compound (3) is oxidized to synthesize a diol derivative, Compound (4), by means of, for example, a common diol-formation reaction with osmium tetraoxide (see *Oxidations in Organic Chemistry*, written by Milos Hudlicky) or a chiral cis-dihydroxylation reaction of Sharpless with AD-mix as a reagent (Sharpless AD) described in *Tetrahedron Asymmetry*, 4(1), 133 (1993), which is incorporated herein by reference.

In this step, as the inert solvent, for example, hydrocarbon type solvents such as benzene, toluene, and hexane; ether type solvents such as tetrahydrofuran, diethyl ether, and 1,2-dimethoxyethane; acetonitrile; acetone; N,N-dimethylformamide; water; a mixture of these solvents; or the like can be employed.

Step 4: Compound (4) is reacted with thionyl chloride in the presence of organic bases such as triethylamine, N-methylmorpholine, diisopropylethylamine, and pyridine, or of inorganic bases such as potassium carbonate and sodium hydrogencarbonate, in an inert solvent, examples of which include hydrocarbon type solvents such as benzene, toluene, and hexane; halogen type solvents such as dichloromethane and chloroform; ether type solvents such as tetrahydrofuran, diethyl ether, and 1,2-dimethoxyethane; acetonitrile; a mixture of these solvents; or the like.

Subsequently, the reaction product is oxidized to synthesize Compound (5), in an inert solvent, examples of which include hydrocarbon type solvents such as benzene, toluene, and hexane; halogen type solvents such as dichloromethane and chloroform; ether type solvents such as tetrahydrofuran, diethyl ether, and 1,2-dimethoxyethane; acetonitrile; acetone; water; a mixture of these solvents; or the like, by employing a common oxidant such as hydrogen peroxide, OXONE® (registered trademark of E.I. Dupont De Nemours and Company), or ruthenium trichloride-sodium metaperiodate (see *Oxidations in Organic Chemistry*, written by Milos Hudlicky).

Step 5: Compound (5) is transformed into Compound (6) by means of the reaction with, for example, sodium azide in an inert solvent, examples of which include ether type solvents such as tetrahydrofuran; ketones such as acetone; N,N-dimethylformamide; water; a mixture of these solvents; or the like.

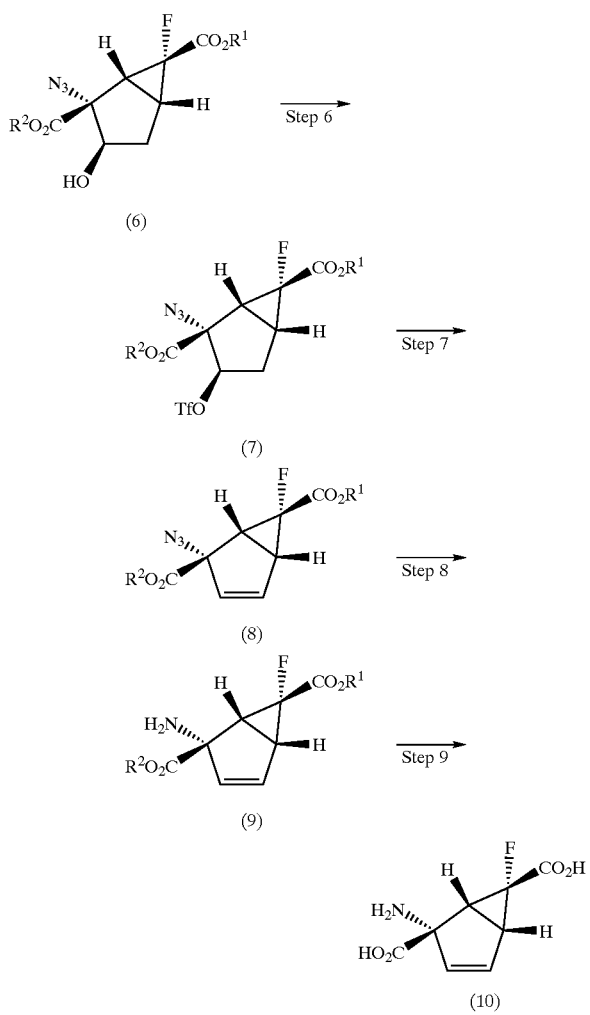

Step 6: Compound (6) is transformed into Compound (7) by means of the reaction with a trifluoromethanesulfonylation agent such as trifluoroacetic anhydride, N-phenyl-bis(trifluoromethanesulfonimide), or the like, in the presence of amines such as triethylamine, diisopropylethylamine, and pyridine, or of inorganic bases such as potassium carbonate and sodium hydrogencarbonate, in an inert solvent, examples of which include hydrocarbon type solvents such as benzene, toluene, and hexane; halogen type solvents such as dichloromethane and chloroform; ether type solvents such as tetrahydrofuran, diethyl ether, and 1,2-dimethoxyethane; acetonitrile; a mixture of these solvents; or the like.

Step 7: Compound (7) is transformed into Compound (8) by means of the reaction with amines such as triethylamine, diisopropylethylamine, pyridine, and 1,8-diazabicyclo [5.4.0]-7-undecene; inorganic bases such as potassium carbonate, sodium hydrogencarbonate, and sodium hydride; or metal alcholates such as sodium methoxide and potassium t-butoxide, in an inert solvent, examples of which include hydrocarbon type solvents such as benzene, toluene, and hexane; halogen type solvents such as dichloromethane and chloroform; ether type solvents such as tetrahydrofuran, diethyl ether, and 1,2-dimethoxyethane; acetonitrile; a mixture of these solvents; or the like.

Step 8: Compound (8) is transformed into Compound (9) by means of a Staudinger reaction with, for example, triethyl phosphite or triphenylphosphine (see *Bull. Chem. Soc. Fr.*, 815 (1985)) or by means of a common reduction reaction of an azide group, utilizing lithium aminoborohydride or the like, described in *Reductions in Organic Synthesis*, written by Ahmed F. Abdel-Magid, which is incorporated herein by reference, in an inert solvent, examples of which include hydrocarbon type solvents such as benzene, toluene, and hexane; halogen type solvents such as dichloromethane and chloroform; ether type solvents such as tetrahydrofuran, diethyl ether, and 1,2-dimethoxyethane; acetonitrile; acetone; water; a mixture of these solvents; or the like.

Step 9: Furthermore, Compound (9) can be transformed into Compound (10) which is the compound of the present invention, by simultaneously or successively converting $R^1$ and $R^2$ of the ester moieties of Compound (9) into hydrogen atoms by means of a common hydrolysis described in *PROTECTIVE GROUPS IN ORGANIC SYNTHESIS*, written by THEODORA W. GREENE and PETER G. M. WUTS, which is incorporated herein by reference.

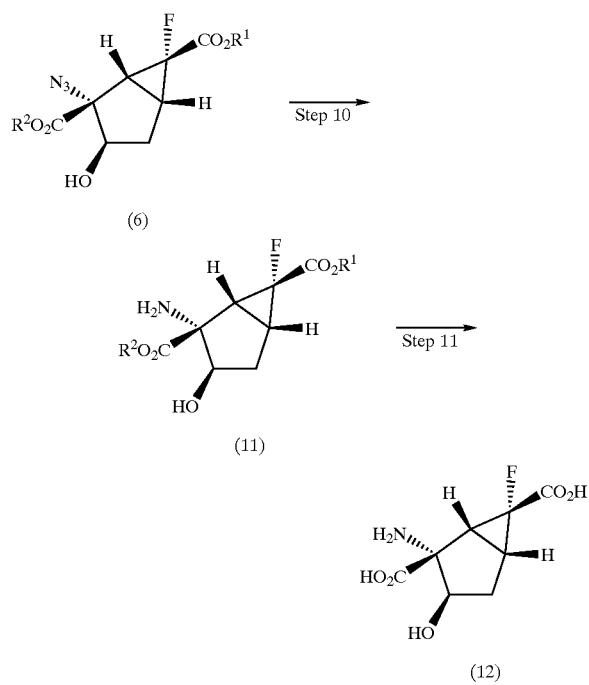

Step 10: On the other hand, Compound (6) can be transformed into Compound (11) which is the compound of the present invention, by means of hydrogenation in the presence of a metal catalyst such as palladium/carbon or palladium black, in an inert solvent, examples of which include alcohols such as ethanol and methanol; esters such as ethyl acetate; N,N-dimethylformamide; water; a mixture thereof; or the like. In this step, when $R^1$ and $R^2$ represent, for example, a benzyl group, or the like, $R^1$ and $R^2$ are hydrogenated during the hydrogenation of the azide group, so that $R^1$ and $R^2$ can be converted into hydrogen atoms.

Step 11: Subsequently, by converting the ester moieties of Compound (11) into carboxylic acids by means of a common hydrolysis described in *PROTECTIVE GROUPS IN ORGANIC SYNTHESIS*, written by THEODORA W. GREENE and PETER G. M. WUTS, which is incorporated herein by reference, Compound (12) which is the compound of the present invention can be synthesized.

The compounds of the present invention can be formulated into pharmaceutical preparations by combining with one or more pharmaceutically acceptable carriers, excipients, and/or diluents. As examples of the carriers, excipients, and diluents described above, mention may be made of water, lactose, dextrose, fructose, sucrose, sorbitol, mannitol, polyethylene glycol, propylene glycol, starch, gum, gelatin, arginate, calcium silicate, calcium phosphate, cellulose, water syrup, methylcellulose, polyvinyl pyrrolidone, alkyl parahydroxybenzoate, talc, magnesium stearate, stearic acid, glycerol, and oils such as sesame oil, olive oil, and soybean oil.

The compounds of the present invention, after being mixed with the carriers, excipients, or diluents, and if necessary, being mixed with additives such as commonly employed fillers, binders, disintegrants, pH regulators, and solubilizers, can be formulated, by means of common formulation technology, into drugs for oral or parenteral administration, especially as group 2 metabotropic glutamate receptor modulators, in the form of, for example, tablets, pills, capsules, granules, powders, liquids, emulsions, suspensions, ointments, injections, and skin plasters. The compounds of the present invention can be administered orally or parenterally to an adult patient in a quantity of 0.01 to 500 mg in a single dose or in divided doses per day, and can be preferably administered orally in view of facility for use and pharmaceutical effects. The dosage can be increased or decreased as appropriate in consideration of the type of disease to be treated and the age, weight, and symptoms of the patient.

BEST MODES FOR CARRYING OUT THE INVENTION

In the following, the present invention is described in detail by presenting Examples and Experimental Examples. It should be understood that the present invention is not restricted to these examples.

EXAMPLE 1

Synthesis of (1R,5R,6R)-6-fluoro-bicyclo[3.1.0]hex-2-ene-2,6-dicarboxylic acid 2-benzyl ester 6-ethyl ester A 2.47 M hexane solution of butyl lithium in an amount of 28.8 mL was added to a solution of 7.83 g of diisopropylamine dissolved in 84 mL of tetrahydrofuran, which was cooled to 0° C. The solution was stirred for 15 minutes, followed by cooling to −62° C. Subsequently, a solution of 12.0 g of ethyl (1R,5R,6R)-6-fluoro-2-oxo-bicyclo[3.1.0] hexane-6-carboxylate dissolved in 40 mL of tetrahydrofuran was added dropwise thereto, while being maintained at −62 to −58° C. One hour later, a solution of 25.3 g of N-phenyl-bis(trifluoromethanesulfonimide) dissolved in 84 mL of tetrahydrofuran was added dropwise thereto over 15 minutes, while maintained at −62 to −60° C. The reaction solution was allowed to naturally warm to room temperature, and was further stirred for one hour. The reaction was quenched with a saturated aqueous solution of sodium hydrogencarbonate, followed by extraction with diethyl ether. The organic layer was washed with water and a saturated aqueous solution of sodium chloride, and was subsequently dried over anhydrous magnesium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=20:1). Immediately, the produced ethyl (1R,5R,6R)-6-fluoro-2-trifluoromethanesulfonyloxy-bicyclo[3.1.0]hex-2-ene-6-carboxylate was dissolved in 195 mL of N,N-dimethylformamide, and 389 mg of palladium acetate, 910 mg of triphenylphosphine, and 12.5 g of benzyl alcohol were added thereto, followed by addition of 11.7 g of triethylamine. Subsequently, the mixture was stirred under a carbon monoxide atmosphere for 4.5 hours at room temperature. 1M hydrochloric acid was added to the reaction mixture, followed by extractions with diethyl ether twice. The organic layers were combined, and the combined organic layer was washed with a saturated aqueous solution of sodium hydrogencarbonate and a saturated aqueous solution of sodium chloride, followed by drying over anhydrous magnesium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=10:1 to 1:1), thereby yielding 6.42 g of (1R,5R,6R)-6-fluoro-bicyclo[3.1.0]hex-2-ene-2,6-dicarboxylic acid 2-benzyl ester 6-ethyl ester.

mp. 90–91° C.

EXAMPLE 2

Synthesis of (1R,2S,3R,5R,6R)-6-fluoro-2,3-dihydroxy-bicyclo[3.1.0]hexane-2,6-dicarboxylic acid 2-benzyl ester 6-ethyl ester AD-mix-β (Aldrich Chemical Company), in an amount of 29.3 g, and methanesulfonamide, in an amount of 5.96 g, were added to 6.36 g of (1R,5R,6R)-6-fluoro-bicyclo[3.1.0]hex-2-ene-2,6-dicarboxylic acid 2-benzyl ester 6-ethyl ester suspended in 150 mL of tert-butanol and 150 mL of water, and the mixture was stirred for 5 days at 4° C. Sodium hydrogensulfite was added to the reaction solution, followed by stirring for 15 minutes at room temperature. Subsequently, water was added thereto, followed by extractions with ethyl acetate three times. The organic layers were combined. The combined organic layer was washed with a saturated aqueous solution of sodium chloride, and was subsequently dried over anhydrous magnesium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=10:1 to 3:2), thereby yielding 4.21 g of (1R,2S,3R,5R,6R)-6-fluoro-2,3-dihydroxy-bicyclo[3.1.0]hexane-2,6-dicarboxylic acid 2-benzyl ester 6-ethyl ester.

$^1$H-NMR (CDCl$_3$) δ1.29 (3H, t, J=7.2 Hz), 2.06–2.21 (2H, m), 2.30 (1H, dd, J=7.6, 2.6 Hz), 2.47 (1H, dd, J=13.2, 7.6 Hz), 2.50 (1H, dd, J=9.2, 1.2 Hz), 4.02 (1H, s), 4.24 (2H, q, J=7.2 Hz), 4.34–4.46 (1H, m), 5.23 (1H, d, J=12.5 Hz), 5.28 (1H, d, J=12.5 Hz), 7.27–7.42 (5H, m).

MS (ESI) m/z; 361 (M+Na)$^+$.

EXAMPLE 3

Synthesis of (1R,1aR,1bS,4aR,5aR)-1-fluoro-3,3-dioxo-tetrahydro-2,4-dioxa-3λ$^6$-thia-cyclopropa[a]pentalene-1,1b-dicarboxylic acid 1b-benzyl ester 1-ethyl ester Thionyl chloride in an amount of 1.70 mL was added to a solution of 3.96 g of (1R,2S,3R,5R,6R)-6-fluoro-2,3-dihydroxy-bicyclo[3.1.0]hexane-2,6-dicarboxylic acid 2-benzyl ester 6-ethyl ester dissolved in 20 mL of methylene chloride, which was cooled to 4° C. Subsequently, the mixture was stirred for 13 hours at 40° C. The solvent and excess reagents were removed under reduced pressure. The residue was dissolved in 12 mL of carbon tetrachloride, 12 mL of acetonitrile, and 20 mL of water. Sodium metaperiodate, in an amount of 3.76 g, and ruthenium trichloride hydrate, in an amount of 50 mg, were added to the solution, and the mixture was stirred for 20 minutes at room temperature. Water was added to the reaction solution, followed by extractions with diethyl ether three times. The organic layers were combined, and the combined organic layer was washed with a saturated aqueous solution of sodium chloride, followed by drying over anhydrous magnesium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=5:1 to 2:1), thereby yielding 4.11 g of (1R,1aR,1bS,4aR,5aR)-1-fluoro-3,3-dioxo-tetrahydro-2,4-dioxa-3λ$^6$-thia-cyclopropa[a]pentalene-1,1b-dicarboxylic acid 1b-benzyl ester 1-ethyl ester.

$^1$H-NMR (CDCl$_3$) δ1.29 (3H, t, J=7.2 Hz), 2.53–2.61 (1H, m), 2.72 (1H, ddd, J=15.2, 7.6, 0.9 Hz), 2.78–2.89 (1H, m), 2.83 (1H, dd, J=7.2, 2.3 Hz), 4.19–4.31 (2H, m), 5.26 (1H, d, J=12.1 Hz), 5.33 (1H, d, J=12.1 Hz), 5.45 (1H, dt, J=7.6, 3.8 Hz), 7.28–7.43 (5H, m). MS (ESI) m/z; 423 (M+Na)$^+$.

EXAMPLE 4

Synthesis of (1R,2R,3R,5R,6R)-2-azide-6-fluoro-3-hydroxy-bicyclo[3.1.0]hexane-2,6-dicarboxylic acid 2-benzyl ester 6-ethyl ester Sodium azide in an amount of 1.09 g was added to 3.73 g of (1R,1aR,1bS,4aR,5aR)-1-fluoro-3,3-dioxo-tetrahydro-2,4-dioxa-3λ$^6$-thia-cyclopropa[a]pentalene-1,1b-dicarboxylic acid 1b-benzyl ester 1-ethyl ester dissolved in 37 mL of N,N-dimethylformamide and 3.7 mL of water, and the mixture was stirred for 14 hours at 50° C. The solvent was removed under reduced pressure, and the residue was dissolved in 187 mL of diethyl ether and 5.2 mL of water. Subsequently, 15 mL of 20% sulfuric acid was added thereto, and the mixture was stirred for 8 hours at room temperature. Water was added to the reaction solution, followed by extractions with diethyl ether three times. The organic layers were combined, and the combined organic layer was washed with a saturated aqueous solution of sodium chloride, followed by drying over anhydrous magnesium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=5:1 to 1:1), thereby yielding 3.02 g of (1R,2R,3R,5R,6R)-2-azide-6-fluoro-3-hydroxy-bicyclo[3.1.0]hexane-2,6-dicarboxylic acid 2-benzyl ester 6-ethyl ester.

$^1$H-NMR (CDCl$_3$) δ1.32 (3H, t, J=7.2 Hz), 2.18–2.54 (5H, m), 4.22–4.36 (1H, m), 4.26 (2H, q, J=7.2 Hz), 5.27 (1H, d, J=12.2 Hz), 5.35 (1H, d, J=12.2 Hz), 7.31–7.45 (5H, m). MS (ESI) m/z; 386(M+Na)$^+$.

EXAMPLE 5

Synthesis of (1R,2S,5R,6R)-2-azide-6-fluoro-bicyclo[3.1.0]hex-3-ene-2,6-dicarboxylic acid 2-benzyl ester 6-ethyl ester Pyridine in an amount of 1.31 g was added to 2.00 g of (1R,2R,3R,5R,6R)-2-azide-6-fluoro-3-hydroxy-bicyclo[3.1.0]hexane-2,6-dicarboxylic acid 2-benzyl ester 6-ethyl ester dissolved in 80 mL of methylene chloride, and the mixture was cooled to −70° C. Trifluoromethanesulfonic anhydride in an amount of 2.33 g was added to the solution, and the mixture was stirred for one hour at 4° C. The reaction mixture was poured into cold water, followed by extractions with diethyl ether three times. The organic layers were combined, and the combined organic layer was washed with a saturated aqueous solution of copper sulfate and a saturated aqueous solution of sodium chloride, followed by drying over anhydrous magnesium sulfate. After the desiccant was filtered off, the filtrate was concentrated under reduced pressure. The residue was dissolved in 15 mL of tetrahydrofuran, and 1.26 g of 1,8-diazabicyclo[5.4.0]-7-undecene was added thereto. The solution was stirred for 5 hours at 50° C., and was stirred for 8 hours at room temperature, followed by dilution with ethyl acetate. The organic layer was washed with 1M hydrochloric acid and a saturated aqueous solution of sodium chloride, and was subsequently dried over anhydrous magnesium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=10:1 to 5:1), thereby yielding 1.39 g of (1R,2S,5R,6R)-2-azide-6-fluoro-bicyclo[3.1.0]hex-3-ene-2,6-dicarboxylic acid 2-benzyl ester 6-ethyl ester.

$^1$H-NMR (CDCl$_3$) δ1.31–1.38 (3H, m), 2.74–2.83 (1H, m), 2.84–2.90 (1H, m), 4.25–4.35 (2H, m), 5.26 (2H, q, J=3.4 Hz), 5.90 (1H, dd, J=5.4, 0.8 Hz), 5.94–6.00 (1H, m), 7.30–7.44 (5H, m). MS (ESI) m/z; 368 (M+Na)$^+$.

EXAMPLE 6

Synthesis of (1R,2S,5R,6R)-2-amino-6-fluoro-bicyclo[3.1.0]hex-3-ene-2,6-dicarboxylic acid 2-benzyl ester 6-ethyl ester Triphenylphosphine supported on a polymer in an amount of 1.21 g (3 mmol/g) was added to 650 mg of (1R,2S,5R,6R)-2-azide-6-fluoro-bicyclo[3.1.0]hex-3-ene-2,6-dicarboxylic acid 2-benzyl ester 6-ethyl ester dissolved in 45 mL of tetrahydrofuran and 5 mL of water, and the mixture was stirred for 9.5 hours at 60° C. After the resin was filtered off, the filtrate was concentrated under reduced pressure. The residue was purified by column chromatography (silica gel: Wako gel C200 (produced by Wako Pure Chemical Industries Ltd.), eluent: hexane-ethyl acetate=5:1 to 1:1), thereby yielding 146 mg of (1R,2S,5R,6R)-2-amino-6-fluoro-bicyclo[3.1.0]hex-3-ene-2,6-dicarboxylic acid 2-benzyl ester 6-ethyl ester.

$^1$H-NMR (CDCl$_3$) δ1.32 (3H, t, J=7.2 Hz), 2.63–2.69 (1H, m), 2.73–2.79 (1H, m), 4.27 (2H, q, J=7.2 Hz), 5.22 (2H, d, J=3.0 Hz), 5.70–5.74 (1H, m), 5.75–5.79 (1H, m), 7.28–7.41 (5H, m). MS (ESI) m/z; 342 (M+Na)$^+$.

EXAMPLE 7

Synthesis of (1R,2S,5R,6R)-2-amino-6-fluoro-bicyclo[3.1.0]hex-3-ene-2,6-dicarboxylic acid Lithium hydroxide hydrate, in an amount of 25 mg, dissolved in 5 mL of water was added to 90 mg of (1R,2S,5R,6R)-2-amino-6-fluoro-bicyclo[3.1.0]hex-3-ene-2,6-dicarboxylic acid 2-benzyl ester 6-ethyl ester dissolved in 2 mL of tetrahydrofuran, and the mixture was stirred for 2 hours at room temperature. The solvent was concentrated under reduced pressure. The residue was purified by ion exchange resin (AG 50W-X8 Resin (H type), eluent: water, a 50% aqueous solution of tetrahydrofuran, and a 10% aqueous solution of pyridine), thereby yielding 24 mg of (1R,2S,5R,6R)-2-amino-6-fluoro-bicyclo[3.1.0]hex-3-ene-2,6-dicarboxylic acid.

mp.>174° C. (decomp.)

EXAMPLE 8

Synthesis of (1R,2R,3R,5R,6R)-2-amino-6-fluoro-3-hydroxy-bicyclo[3.1.0]hexane-2,6-dicarboxylic acid 10% palladium/carbon in an amount of 15 mg was added to 218 mg of (1R,2R,3R,5R,6R)-2-azide-6-fluoro-3-hydroxy-bicyclo[3.1.0]hexane-2,6-dicarboxylic acid 2-benzyl ester 6-ethyl ester dissolved in 2.5 mL of acetic acid and 0.5 mL of water. Subsequently, the mixture was stirred under a hydrogen atmosphere for 12 hours at room temperature. After the catalyst was filtered off, the filtrate was concentrated under reduced pressure. The residue was dissolved in 7.8 mL of 10% hydrochloric acid, and the mixture was refluxed by heating for 1 hour. The solvent was removed under reduced pressure. The residue was purified by ion exchange resin (AG 50W-X8 Resin (H type), eluent: water, a 50% aqueous solution of tetrahydrofuran, and a 10% aqueous solution of pyridine), thereby yielding 104 mg of (1R,2R,3R,5R,6R)-2-amino-6-fluoro-3-hydroxy-bicyclo[3.1.0]hexane-2,6-dicarboxylic acid.

mp.>172° C. (decomp.)

Experimental Example (Effects of Test Compounds on cAMP Accumulation)

CHO cells stably expressing metabotropic glutamate receptors mGluR2 were seeded in a 96-well plate in the ratio of $1.26 \times 10^4$ cells/well/0.32 cm$^2$/150 µl in Dalbeco-modified Eagle medium [1% proline, 50 units/ml penicillin, 50 µg/ml streptomycin, 2 mM L-glutamine (added when used)] containing 10% dialyzed fetal bovine serum, and were cultured for 2 days at 37° C. under an atmosphere of 5% $CO_2$. Subsequently, the medium was replaced with an L-glutamine free medium. Four hours later, the supernatant liquid was aspirated. PBS(+)-IBMX (10 mM PBS(–), 1 mM $MgCl_2$, 1 mM $CaCl_2$, 1 mM IBMX) in an amount of 150 µl was added thereto, followed by incubation for 20 minutes at 37° C. in the presence of 5% $CO_2$. The supernatant liquid was again aspirated. Subsequently, 60 µl of $10^{-5}$ M Forskolin, 30 µM glutamic acid, and PBS(+)-IBMX containing $10^{-10}$ to $10^{-4}$ M test compounds were added thereto, followed by incubation for 15 minutes at 37° C. in the presence of 5% $CO_2$. A study was carried out for the antagonistic effects of the test compounds on the Forskolin stimulation cAMP accumulation quantity suppression [for control, the conditions were set with no addition of the compounds (Tanabe et al., Neuron, 8, 169–179 (1992))]. The reactions were quenched by adding 100 µl of ice-cooled ethanol, the entire quantity of the supernatant liquid was collected in a separate plate, and was subsequently dried up at normal temperature with an evaporator, followed by preservation at –20° C. In the dried-up samples, the quantity of cAMP was measured using a cAMP EIA kit (from the Amasham company). The control value was subtracted from each cAMP quantity. The concentrations of the test compounds, at which the suppression by 30 µM glutamic acid with respect to cAMP increased due to stimulation effected by $10^{-5}$ M Forskolin was inhibited 50%, which were determined as $IC_{50}$ value, were obtained.

The compounds of the present invention exhibited low $IC_{50}$ values in the measurement described in the present Experimental Example.

(1R,2R,3R,5R,6R)-2-amino-6-fluoro-3-hydroxy-bicyclo [3.1.0]hexane-2,6-dicarboxylic acid described in Example 8 of the present invention exhibited $IC_{50}$=476 nM in the measurement described in the present Experimental Example.

Industrial Applicability

According to the present invention, modulators acting on metabotropic glutamate receptors can be provided.

Therefore, the present invention is useful for the treatment and/or prevention of psychiatric disorders such as schizophrenia, anxiety and its associated diseases, depression, bipolar disorder, and epilepsy; and/or on neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

What is claimed is:

1. A 2-amino-6-fluoro-bicyclo[3.1.0]hexane-2,6-dicarboxylic acid compound having a relative stereochemical configuration represented by the formula:

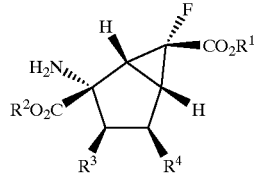

[1]

(wherein, $R^1$ and $R^2$ are the same or different, and each represents a hydrogen atom, a $C_{1-10}$ alkyl group, a $C_{3-8}$ cycloalkyl group, a $C_{3-8}$ cycloalkyl $C_{1-6}$ alkyl group, an aryl group, an aryl $C_{1-6}$ alkyl group, a $C_{1-6}$ alkoxy $C_{1-6}$ alkyl group, an $C_{1-6}$ hydroxyalkyl group, a $C_{1-6}$ alkylthio $C_{1-6}$ alkyl group, a $C_{1-6}$ mercaptoalkyl group, a tetrahydrofuranyl group, or a tetrahydropyranyl group;

in $R^3$ and $R^4$, when $R^3$ is a hydroxyl group, $R^4$ is a hydrogen atom; alternatively, $R^3$ and $R^4$ together form a C—C single bond), a pharmaceutically acceptable salt thereof, or a hydrate thereof.

2. The compound, the pharmaceutically acceptable salt thereof, or the hydrate thereof, according to claim 1, wherein $R^3$ is a hydroxyl group, and $R^4$ is a hydrogen atom, in the formula [I] described above.

3. The compound, the pharmaceutically acceptable salt thereof, or the hydrate thereof, according to claim 1, wherein $R^3$ is a hydroxyl group, and $R^1$, $R^2$, and $R^4$ are each a hydrogen atom, in the formula [I] described above.

4. The compound according to claim 3, which is (1R,2R, 3R,5R,6R)-2-amino-6-fluoro-3-hydroxy-bicyclo[3.1.0] hexane-2,6-dicarboxylic acid, the pharmaceutically acceptable salt thereof, or the hydrate thereof.

5. A pharmaceutical composition comprising the compound according to claim 1 as an active ingredient.

6. A pharmaceutical composition according to claim 5, that is a group 2 metabotropic glutamate receptor modulator.

* * * * *